US010465210B2

(12) United States Patent
Jung et al.

(10) Patent No.: US 10,465,210 B2
(45) Date of Patent: Nov. 5, 2019

(54) RECOMBINANT PROTEIN, RECOMBINANT MICROORGANISM, AND METHOD OF DEGRADING MACROMOLECULAR SUBSTANCE

(71) Applicant: Samsung Electronics Co., Ltd, Suwon-si, Gyeonggi-do (KR)

(72) Inventors: Yukyung Jung, Hwaseong-si (KR); Taeyong Kim, Daejeon (KR); Seunghoon Song, Yongin-si (KR); Jiae Yun, Hwaseong-si (KR); Jinhwan Park, Suwon-si (KR); SunJung Byun, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 15/724,979

(22) Filed: Oct. 4, 2017

(65) Prior Publication Data

US 2018/0094284 A1 Apr. 5, 2018

(30) Foreign Application Priority Data

Oct. 4, 2016 (KR) .................. 10-2016-0127547

(51) Int. Cl.
| | | |
|---|---|---|
| *C12N 9/02* | (2006.01) | |
| *C12P 5/02* | (2006.01) | |
| *C12N 15/00* | (2006.01) | |
| *C12N 1/20* | (2006.01) | |
| *C07H 21/04* | (2006.01) | |
| *C12P 7/24* | (2006.01) | |

(52) U.S. Cl.
CPC .............. *C12P 7/24* (2013.01); *C12N 9/0069* (2013.01); *C12N 9/0071* (2013.01); *C12P 5/02* (2013.01); *C12Y 113/12016* (2013.01); *C12Y 114/14005* (2013.01); *C12Y 114/14009* (2013.01); *C12Y 114/99* (2013.01)

(58) Field of Classification Search
None
See application file for complete search history.

(56) References Cited

U.S. PATENT DOCUMENTS

| 9,796,993 B2* | 10/2017 | Chen-Sarkanen ...... C12P 19/00 |
| 2006/0106120 A1 | 5/2006 | Abe et al. |
| 2014/0335571 A1* | 11/2014 | Chen-Sarkanen ...... C12P 19/00 |
| | | 435/99 |

FOREIGN PATENT DOCUMENTS

| CN | 103980535 A | 8/2014 |
| JP | 2006-008780 B2 | 12/2006 |

OTHER PUBLICATIONS

Lapidus. YOAI_BACSU. UniProtKB Database. 2009.*
LaVallie. Production of Recombinant Proteins in *Escherichia coli*. Current Protocols in Protein Science (1995) 5.1.1-5.1.8.*
Jeon et al., "Functional analysis of alkane hydroxylase system derived from *Pseudomonas aeruginosa* E7 for low molecular weight polyethylene biodegradation", *International Biodeterioration & Biodegradation*, 103: 141-146 (2015).
Sharma et al., Degradation assessment of low density polyethylene (LDP) and polyethylene (PP) by an indigenous isolate of *Pseudomonas stutzeri*, *Journal of Scientific & Industrial Research*, 63: 293-296 (2004).
Skariyachan et al., Novel bacterial consortia isolated from plastic garbage processing areas demonstrated enhanced degradation for low density polyethylene, *Environ. Sci. Pollut. Res.*, DOI 10.1007/s113560-016-700-y; pp. 1-13 (2016).
Yang et al., "Evidence of Polyethylene Biodegradation by Bacterial Strains from the Guts of Plastic-Eating Waxworms", *Environmental Science & Technology*, 48: 13776-13784 (2014).
Yang et al., "Complete genome sequence of *Bacillus* sp. YP1, a polyethylene-degrading bacterium from waxworm's gut", *Journal of Biotechnology*, 200:77-78 (2015).
Yoon et al., "Biodegradation of Polyethylene by a Soil Bacterium and AlkB Cloned Recombinant Cell", *Journal Bioremediation & Biodegradation*, 3(4): 1-8 (2012).

* cited by examiner

*Primary Examiner* — Yong D Pak
(74) *Attorney, Agent, or Firm* — Leydig, Voit & Mayer, Ltd.

(57) ABSTRACT

Provided are a recombinant protein, a gene encoding the recombinant protein, a recombinant microorganism including the gene, and a method of degrading a macromolecular substance using the recombinant microorganism or the recombinant protein.

8 Claims, 2 Drawing Sheets

Specification includes a Sequence Listing.

RECOMBINANT PROTEIN, RECOMBINANT MICROORGANISM, AND METHOD OF DEGRADING MACROMOLECULAR SUBSTANCE

CROSS-REFERENCE TO RELATED APPLICATION

This application claims the benefit of Korean Patent Application No. 10-2016-0127547, filed on Oct. 4, 2016, in the Korean Intellectual Property Office, the disclosure of which is incorporated herein in its entirety by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 36,664 Byte ASCII (Text) file named "728237_ST25.TXT," created on Oct. 4, 2017.

BACKGROUND

1. Field

The present disclosure relates to a recombinant protein, a gene encoding the recombinant protein, a recombinant microorganism, and a method of degrading a macromolecular substance.

2. Description of the Related Art

Macromolecular materials, otherwise known as plastics, have gradually replaced conventional materials, such as glass, metal, paper, wood, and stone in various applications ranging from industrial materials to disposable consumables. The disposal of used plastic waste depends on incineration or landfills. However, due to leakage of hormones into the environment and incomplete combustion of waste from which toxic dioxin is detected, used plastic waste causes serious problems in terms of environmental pollution of soil, rivers, and the atmosphere.

In order to solve these problems, there is great pressure to put biodegradable or biointegrable plastics into practical use and obligate their usage. Thus, in countries including the United States, Japan, Germany, and Italy, biodegradable plastics have actively been put into practical use. For example, there is a requirement to use biodegradable macromolecular materials in various plastic products. Currently, the most widely used synthetic plastics in the industry are polyethylene (PE), polyurethane (PUR), nylon, and polyvinylalcohol (PVA). To promote decomposition of such synthetic plastics, methods including photolysis, pyrolysis, and biodegradation are used. Photolysis induces oxidation of a macromolecular material by using ultraviolet rays of sunlight. Pyrolysis changes properties of a macromolecular material through application of heat thereto. Biodegradation is degradation of macromolecular materials by aerobic or anaerobic microorganisms.

Among the above-mentioned decomposition methods, biodegradation by microorganisms is the most efficient. However, there is a need to develop new microorganisms and methods to efficiently degrade macromolecular materials. This invention provides such microorganisms and methods.

SUMMARY

Provided is a recombinant protein including an amino acid sequence having at least 95% sequence identity to one of SEQ ID NOs: 1, 2, 3, 4, 5, 6, or 7, and a gene including a nucleotide sequence encoding same.

Also provided is a recombinant microorganism that expresses or includes a recombinant protein at an increased level relative to a parent strain, the protein including an amino acid sequence having at least 95% sequence identity to one of SEQ ID NOs: 1, 2, 3, 4, 5, 6, or 7.

Further provided is a method of degrading a macromolecular substance, the method including contacting the macromolecular substance with a recombinant microorganism, a lysate thereof, or a fraction of the lysate thereof, the recombinant microorganism that expresses or includes a recombinant protein including an amino acid sequence having at least 95% sequence identity to one of SEQ ID NOs: 1, 2, 3, 4, 5, 6, or 7.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
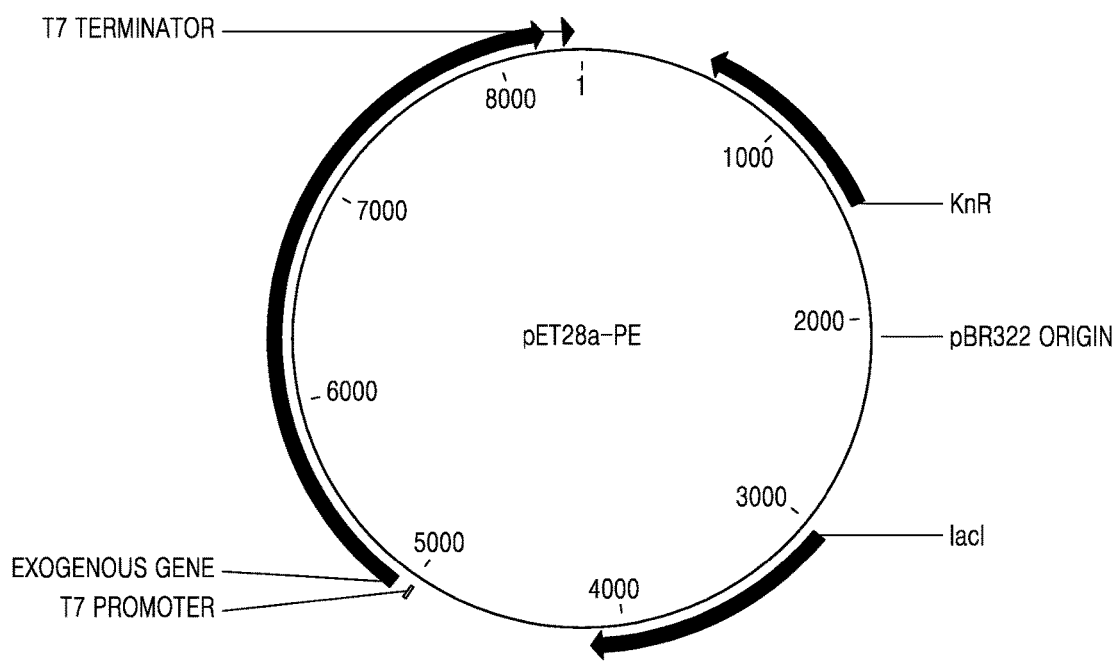
FIG. 1 shows a vector map of pET28a-PE.
Figure 2:
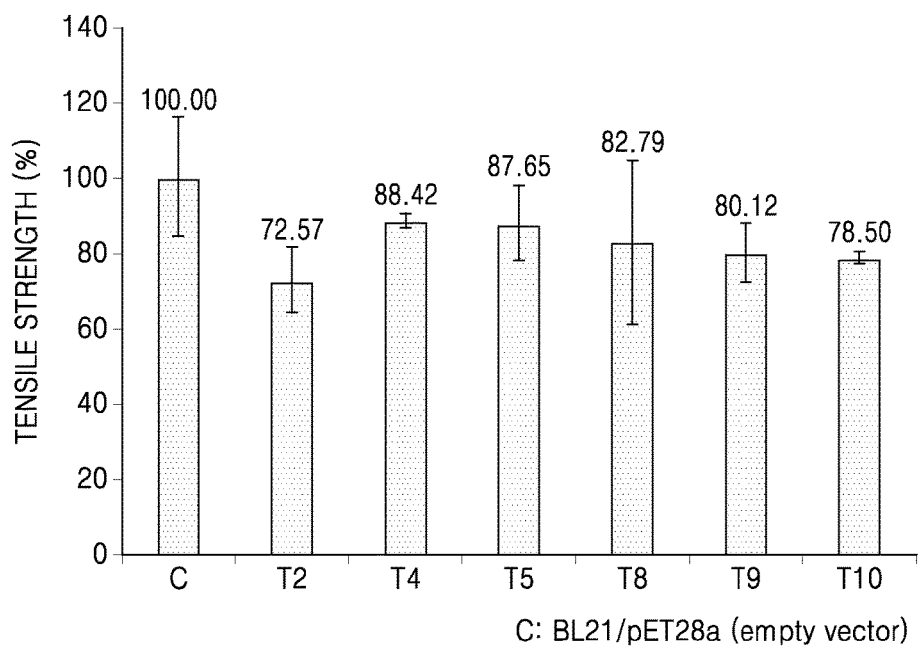
FIG. 2 shows a graph confirming that crude extracts containing T2, T4, T5, T8, T9, and T10 proteins reduce tensile strength of polyethylene.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects. Expressions such as "at least one of," when preceding a list of elements, modify the entire list of elements and do not modify the individual elements of the list.

The term "gene" as used herein refers to a nucleic acid that expresses a specific protein or polypeptide, and may include a sequence associated with a coding region and a regulatory sequence associated with regions other than the coding region, such as a 5'-non coding sequence and 3'-non coding sequence. A regulatory region of the gene may include a promoter, an enhancer, an operator, a ribosome-binding site, a polyA-binding site, and a terminator region.

The term "sequence identity" as used herein in connection with a polynucleotide or polypeptide refers to a degree of sameness of bases or amino acid residues of two sequences after aligning the two sequences to a maximum match in a particular comparison region. The sequence identity is a value obtained by comparing two sequences that are optimally aligned in a specific comparison region. A part of sequences in a comparison region may be added or deleted in comparison with a reference sequence. The sequence identity (%) may be, for example, calculated by comparing sequences that are optimally aligned throughout a comparison region, by determining the number of positions at which the same amino acids or nucleotide nucleotides appear in both sequences to obtain the number of matched positions between the two sequences, dividing the number of the matched positions by the total number of positions in a comparison range, i.e., dividing the number of the matched positions by a range size, and multiplying the result by 100 to obtain sequence identity as a percentage. The sequence identity (%) may be determined using known sequence comparison programs, and examples of such programs include BLASTN or BLASTP (NCBI), CLC Main Workbench (CLC bio), and MegAlign™ (DNASTAR Inc).

Sequence identity of several levels may be used in identifying a polypeptide or polynucleotide of different species having the same or similar functions or activities. For example, a polypeptide or polynucleotide of one species may have at least 50%, at least 55%, at least 60%, at least 65%, at least 70%, at least 75%, at least 80%, at least 85%, at least 90%, at least 95%, at least 96%, at least 97%, at least 98%, at least 99%, or at least 100% sequence identity to a polypeptide or polynucleotide of another species.

The term "increase in activity", "increased activity", or "increased level" as used herein refers to a detectable increase in activity of a cell, polypeptide, protein, or enzyme relative to the activity of a cell, polypeptide, protein, or enzyme of the same type that does not have a given genetic modification (for example, a parent cell or a native or "wild-type" cell, polypeptide, protein, or enzyme). The term "cell activity" as used herein refers to activity of a specific polypeptide, protein, or enzyme of a cell. For example, the activity of the modified or engineered cell, polypeptide, protein, or enzyme may be increased by about 5%, about 10%, about 15%, about 20%, about 30%, about 50%, about 60%, about 70%, or about 100% relative to the activity of a cell, polypeptide, protein, or enzyme of the same type that does not have a given modification or has not been engineered, such as a wild-type cell, polypeptide, protein, or enzyme. Cells having increased activity of a polypeptide, protein, or enzyme may be confirmed by using any method known in the art. Cells having increased activity may have undergone genetic engineering for increasing activity of at least one enzyme or polypeptide thereof, as compared with cells that have not undergone genetic engineering.

One aspect provides a recombinant protein including an amino acid sequence having at least 95% sequence identity to one of SEQ ID NOs: 1, 2, 3, 4, 5, 6, or 7.

The recombinant protein may be a recombinant protein including an amino acid sequence having at least 95%, 96%, 97%, 98%, or 99% sequence identity to SEQ ID NO: 1; a recombinant protein including an amino acid sequence having at least 95%, 96%, 97%, 98%, or 99% sequence identity to SEQ ID NO: 2; a recombinant protein including an amino acid sequence having at least 95%, 96%, 97%, 98%, or 99% sequence identity to SEQ ID NO: 3; a recombinant protein including an amino acid sequence having at least 95%, 96%, 97%, 98%, or 99% sequence identity to SEQ ID NO: 4; a recombinant protein including an amino acid sequence having at least 95%, 96%, 97%, 98%, or 99% sequence identity to SEQ ID NO: 5; a recombinant protein including an amino acid sequence having at least 95%, 96%, 97%, 98%, or 99% sequence identity to SEQ ID NO: 6; or a recombinant protein including an amino acid sequence having at least 95%, 96%, 97%, 98%, or 99% sequence identity to SEQ ID NO: 7. In addition, a recombinant protein including an amino acid sequence having at least 95% sequence identity to one of SEQ ID NOs: 1, 2, 3, 4, 5, 6, or 7 may include a protein having a same function as a protein having an amino acid sequence of one of SEQ ID NOs: 1, 2, 3, 4, 5, 6, or 7, and a modification such as substitution, deletion, or insertion of at least one amino acid, or a combination thereof. Also provided is a combination of such proteins.

The recombinant protein may have activity of an oxygenase. The oxygenase refers to an enzyme that catalyzes oxidation (i.e., a reaction in which an oxygen atom binds to a substrate) and may be an enzyme that adds a carbonyl group to a macromolecular substance, adds a carbon-oxygen bond to a macromolecular substance, or oxidizes a carbon-oxygen bond or carbon-carbon bond of a macromolecular substance. The recombinant protein may act on a carbon-hydrogen bond or carbon-carbon bond of a macromolecular substance. For example, the recombinant protein may catalyze conversion of a carbon-hydrogen bond or carbon-carbon bond of a macromolecular substance to a carbon-oxygen bond, i.e., a carbonyl group, of a macromolecular substance. In some embodiments, the recombinant protein may be an enzyme classified as EC.1.13, or EC.1.14, such as an enzyme classified as EC. 1.14.14.9, EC. 1.13.12.16, EC. 1.14.14.5, or EC. 1.14.99.48.

The recombinant protein may be from a microorganism belonging to the genus *Bacillus*. The microorganism belonging to the genus *Bacillus* may be the *Bacillus* YP1.

Another aspect provides a gene including a nucleotide sequence encoding any of the recombinant proteins described herein. In one embodiment, the gene may include a nucleotide sequence encoding a recombinant protein including an amino acid sequence having at least 95% sequence identity to one of SEQ ID NOs: 1, 2, 3, 4, 5, 6, or 7.

In one embodiment, the polynucleotide including the nucleotide sequence may be codon-optimized for a particular recombinant microorganism. The expression "codon-optimized" as used herein indicates that a gene configured to encode the same amino acid is produced, but at least one codon thereof is substituted with a codon that is favorable for expression in the particular microorganism.

The gene may include at least one nucleotide sequence selected from the group consisting of nucleotide sequences of SEQ ID NOs: 8 to 14. A nucleotide sequence encoding a recombinant protein that includes an amino acid sequence having at least 95% sequence identity to SEQ ID NO: 1 may include a nucleotide sequence of SEQ ID NO: 8. A nucleotide sequence encoding a recombinant protein that includes an amino acid sequence having at least 95% sequence identity to SEQ ID NO: 2 may include a nucleotide sequence of SEQ ID NO: 9. A nucleotide sequence encoding a recombinant protein that includes an amino acid sequence having at least 95% sequence identity to SEQ ID NO: 3 may include a nucleotide sequence of SEQ ID NO: 10. A nucleotide sequence encoding a recombinant protein that includes an amino acid sequence having at least 95% sequence identity to SEQ ID NO: 4 may include a nucleotide sequence of SEQ ID NO: 11. A nucleotide sequence encoding a recombinant protein that includes an amino acid sequence having at least 95% sequence identity to SEQ ID NO: 5 may include a nucleotide sequence of SEQ ID NO: 12. A nucleotide sequence encoding a recombinant protein that includes an amino acid sequence having at least 95% sequence identity to SEQ ID NO: 6 may include a nucleotide sequence of SEQ ID NO: 13. A nucleotide sequence encoding a recombinant protein that includes an amino acid sequence having at least 95% sequence identity to SEQ ID NO: 7 may include a nucleotide sequence of SEQ ID NO: 14.

Another aspect provides an expression vector including any one of the polynucleotides or genes described herein. Any vector that may be used to introduce a polynucleotide or gene into a microorganism may be used herein. The gene or polynucleotide optionally includes a restriction enzyme site that cooperates with a vector to be inserted, and thus may be effectively cloned into an expression vector. To express the recombinant protein, such an expression vector may optionally include a promoter sequence, a translation initiation sequence, and a translation termination sequence. The vector may be a plasmid or a viral vector.

Another aspect provides a recombinant microorganism that expresses or includes a protein as described herein, or a combination of such proteins (e.g., a protein including an amino acid sequence having at least 95% sequence identity to one of SEQ ID NOs: 1, 2, 3, 4, 5, 6, and/or 7 at an increased level relative to a parent strain).

The recombinant microorganism may have increased activity of an oxygenase relative to a parent strain. The recombinant microorganism may have a genetic modification to produce a recombinant protein that degrades a bond of a macromolecular substance upon oxidation. The genetic modification may include an exogenous or foreign (heterologous) gene or polynucleotide encoding a protein with oxygenase activity as described herein.

The recombinant microorganism may include a gene that encodes a recombinant protein at an increased copy number relative to a parent strain, the protein including an amino acid sequence having at least 95% sequence identity to one of SEQ ID NOs: 1, 2, 3, 4, 5, 6, or 7.

The recombinant microorganism may include at least one gene encoding a protein or a combination thereof, the protein including an amino acid sequence having at least 95% sequence identity to one of SEQ ID NOs: 1, 2, 3, 4, 5, 6, or 7. For example, the recombinant microorganism may include at least two, three, four, five, ten, or fifty genes encoding a protein having at least 95% sequence identity to one of SEQ ID NOs: SEQ ID NOs: 1, 2, 3, 4, 5, 6, and/or 7. When the recombinant microorganism includes a plurality of genes, each of the plurality of genes may be identical to or different from each other, or may encode the same or different proteins having at least 95% sequence identity to one of SEQ ID NOs: 1, 2, 3, 4, 5, 6, or 7. The at least one gene may be an exogenous gene that is integrated into the genome of the microorganism or may remain independent from the genome of the microorganism.

The gene may include a nucleotide sequence selected from the group consisting of nucleotide sequences of SEQ ID NOs: 8 to 14. The amino acid sequences of SEQ ID NOs: 1 to 7, the nucleotide sequences of SEQ ID NOs: 8 to 14, and the recombinant protein are the same as described above.

Regarding the recombinant microorganism, the gene may be introduced into the microorganism by any method known in the art, for example, transformation, electroporation, or the like.

The recombinant microorganism may be bacteria, yeast, or fungi. The bacteria may be gram-positive or gram-negative. The gram-negative bacteria may belong to the genus *Escherichia*, the genus *Xanthomonas*, genus *Xanthobacter*, the genus *Salmonellar*, or the genus *Pseudomonas*. The microorganism belonging to the genus *Escherichia* may be *E. coli*. The gram-positive bacteria may belong to the genus *Corynebacterium* or the genus *Bacillus*. The bacteria may belong to the genus *Saccharomyces*. The protein may be produced in large quantities using the recombinant microorganism.

Another aspect provides a composition for degrading a macromolecular substance including any recombinant microorganism described herein, a lysate thereof, or a fraction of the lysate thereof, the microorganism expressing or including a recombinant protein including an amino acid sequence having at least 95% sequence identity to one of SEQ ID NOs: 1, 2, 3, 4, 5, 6, or 7.

The microorganism may be a recombinant microorganism expressing or including a protein or a combination thereof at an increased level relative to a parent strain, the protein including an amino acid sequence having at least 95% sequence identity to one of SEQ ID NOs: 1, 2, 3, 4, 5, 6, or 7.

The recombinant microorganism may include a gene encoding a protein or a combination thereof at an increased copy number relative to a parent strain, the protein including an amino acid sequence having at least 95% sequence identity to one of SEQ ID NOs: 1, 2, 3, 4, 5, 6, or 7. The gene may include at least one nucleotide sequence selected from the group consisting of nucleotide sequences of SEQ ID NOs: 8 to 14.

The composition may degrade a macromolecular substance. The composition may catalyze degradation of a macromolecular substance. The composition may catalyze oxidation or conversion of a carbon-hydrogen or carbon-carbon bond to a carbon-oxygen bond, i.e., a carbonyl group, of a macromolecular substance. Degradation may refer to division of a macromolecular substance into units similar to that of a repeat unit of the macromolecular substance, or reduction of force or intensity applied to a macromolecular substance required for breakage of a macromolecular substance. Here, the force or intensity applied required for the breakage may be measured by tensile strength, which may be measured by methods known in the art. For example, the tensile strength may be measured by using a texture analyzer, a universal testing machine, or an injection machine. In addition, degradation may refer to a decrease in a molecular weight, a mass, a weight, crystallinity, a thickness of a crystal layer, a melting temperature, an average size of crystals, or an increase in an amount of small crystals, each of which may be measured by methods known in the art.

The term "macromolecule" as used herein refers to a polymer or a copolymer.

The macromolecular substance may include a polyalkylene, a polyacrylic acid, and/or a polystyrene.

The macromolecular substance may have a weight average molecular weight (MW) in a range of about 10,000 Da to about 300,000 Da, about 50,000 Da to about 250,000 Da, about 100,000 Da to about 200,000 Da, or about 130,000 Da to about 180,000 Da. The MW may be measured by conventional method of measuring the molecular weight of a polymer. A macromolecular substance including a polyalkylene may include an alkylene repeat unit of 1 to 10 carbon atoms. For example, the number of carbon atoms of the alkylene repeat unit in the macromolecular substance may be in a range of 2 to 8, 2 to 6, or 2 to 4. The repeat unit may include ethylene, propylene, or butylene. The macromolecular substance may include, for example, polyethylene, polypropylene, or polybutylene. Polyethylene may be a macromolecular substance that is very stable and synthesized by polymerization of ethylene monomers. In some embodiments, the recombinant protein including an amino acid sequence having at least 95% sequence identity to one of SEQ ID NOs: 1, 2, 3, 4, 5, 6, or 7, and/or recombinant microorganism expressing or including same may biodegrade the macromolecular substance without the need for additional steps such as UV degradation, pyrolysis, photolysis, or chemical degradation using strong acids.

Another aspect provides a method of degrading a macromolecular substance, the method including contacting a macromolecular substance with a recombinant microorganism, a lysate thereof, or a fraction of the lysate thereof, wherein the microorganism expresses or includes a protein including an amino acid sequence having at least 95% sequence identity to one of SEQ ID NOs: 1, 2, 3, 4, 5, 6, or 7. All aspects of the microorganisms, macromolecular substance, and other aspects of the method are as previously described.

The microorganism may be a recombinant microorganism including a protein or a combination thereof at an increased level relative to a parent strain, the protein including an amino acid sequence having at least 95% sequence identity to one of SEQ ID NOs: 1, 2, 3, 4, 5, 6, and/or 7. The recombinant microorganism may include a gene encoding a protein including an amino acid sequence having at least 95% sequence identity to one of SEQ ID NOs: 1, 2, 3, 4, 5, 6, or 7. The gene may include at least one nucleotide sequence selected from the group consisting of nucleotide sequences of SEQ ID NOs: 8 to 14.

The lysate refers to a state in which the microorganism is broken up so that contents thereof are exposed to the outside of a cell. The lysate may be obtained by breaking up a cell by using an enzyme, heat, or pressure. The lysate may include the recombinant microorganism extract, recombinant protein extract, or crude extracts thereof.

The fraction of the lysate may be obtained by separation from a material dissolved in an aqueous or oily solvent.

The contact may be in liquid or solid form. The contact may be performed by, for example, contacting the macromolecular substance with a microorganism cultured in a medium, a culture of the microorganism, a lysate of the microorganism and/or the culture, or a fraction of the lysate.

The contact may be liquid-liquid and/or liquid-solid contact which is contact of the macromolecular substance with the microorganism, a culture of the microorganism, a lysate of the microorganism and/or the culture, or a fraction of the lysate. The liquid-liquid and/or liquid-solid contact may include mixed contact. The contact may be performed in a sealed container or an open container. The term "sealed" as used herein refers to a state substantially or completely fastened or closed securely (e.g., air-sealed, liquid-sealed, liquid-tight, air-tight, or combination thereof depending on the nature of the sample). The contact may be performed in an anaerobic or aerobic condition. The contact may be performed when the growth stage of the microorganism is in an exponential phase or a stationary phase.

The contact may include culturing or incubating the microorganism while contacting the microorganism with a sample containing the macromolecular substance. The contact may be performed under conditions in which the microorganism can survive in a sealed container. The conditions in which the microorganism can survive may include a condition in which the microorganism proliferates or a condition that maintains the microorganism in a resting state. The culturing may be performed under conditions suitable for proliferating the microorganism. The culturing may refer to culturing under conditions for culturing the microorganism. The conditions for culturing the microorganism include, for example, a carbon source, nitrogen source, or oxygen source condition used for the strain. The carbon source may include a monosaccharide, a disaccharide, or a polysaccharide. The carbon source may include glucose, fructose, sucrose, mannitol, mannose, maltose, lactose, xylose, glycerol, sorbitol, cellobiose, ethanol, or galactose. The nitrogen source available for the microorganism may include an organic nitrogen compound or an inorganic nitrogen compound. The nitrogen source may include, for example, an amino acid, an amide, an amine, a nitrate, or an ammonium salt. The medium used for culturing the microorganism may include any conventional medium suitable for the growth of a host cell, and an example thereof is a minimal or complex medium containing appropriate supplements. Such a suitable medium may be available from a commercial vendor or may be prepared according to methods known in the art. The medium used for the culturing may be a medium that can satisfy the requirements of the microorganism. The medium may include a medium selected from the group consisting of a carbon source, a nitrogen source, a salt, a trace element, and a combination thereof. The culturing may be performed under aerobic conditions. A temperature at which the culturing is performed may be in a range of about 15° C. to about 35° C. A pH of the culture medium may be in a range of about 4 to about 8. The culturing may be static culturing or stirring culturing.

The contact may be performed in a batch manner or in a continuous manner. The contact may include, for example, contacting the contacted macromolecular substance obtained from the degradation with a recombinant microorganism having increased oxygenase activity relative to a parent strain, a lysate of the recombinant microorganism, or a fraction of the lysate, wherein the recombinant microorganism may include a recombinant microorganism including an exogenous gene that encodes a protein having oxygenase activity.

The contact with the recombinant microorganism, a lysate thereof, or a fraction of the lysate may be performed once or two or more times, for example, 2, 3, 5, 10, or more times. The contact may be continued or repeated until a desired repeat unit of the macromolecular substance is obtained. The contact may be performed for about 1 to about 15 days, about 2 to about 14 days, about 3 to about 12 days, about 4 to about 10 days, about 5 to about 9 days, or about 6 to about 8 days.

In the method, for one contact of the macromolecular substance, the macromolecular substance may be applied as a degradation subject in an amount ranging from about 1 mg to about 500 mg, about 2 mg to about 250 mg, about 5 mg to about 100 mg, about 10 mg to about 50 mg, about 20 mg to about 40 mg, or about 25 mg to about 35 mg.

In the method, the contact may be performed under conditions of pH in a range of about 4 to about 10, about 5 to about 9, about 6 to about 8, or about 7 to about 8.

The microorganism, a lysate of the microorganism, or a fraction of the lysate may include a recombinant protein in an amount ranging from about 10 mg to about 200 mg, about 15 mg to about 150 mg, about 16 mg to about 120 mg, or about 17 mg to about 110 mg.

The amino acid sequences of SEQ ID NOs: 1 to 7, the nucleotide sequences of SEQ ID NOs: 8 to 14, the recombinant protein, the degradation, and the macromolecular substance are the same as described above.

In various embodiments, the recombinant microorganism may be used to remove a macromolecular substance. The term "remove" as used herein refers to reduction of the amount of the macromolecular substance. The reduction may include partial or complete removal of the macromolecular substance.

The following further illustrate the invention but, of course, should not be construed as in any way limiting its scope.

Example 1: Recombinant *E. coli* Expressing Polypeptides of SEQ ID NOs: 1 to 7, and Degradation of a Macromolecular Substance Using the Same In Example 1, recombinant *E. coli* strains expressing polypeptides of SEQ ID NOs: 1 to 7, respectively, were prepared, and an effect of degradation of polyethylene was confirmed using the recombinant *E. coli*.

(1) Preparation of Recombinant *E. coli* that Expresses Polypeptides of SEQ ID NOs: 1 to 7

All of genes derived from *Bacillus* sp. YP1 were prepared by synthesizing DNA to be optimized for codons of *E. coli* (Cosmogenetech). PCR was performed by using DNA synthesized herein as a template, and a primer set of nucleotide sequences of SEQ ID NOs: 15 and 16, a primer set of nucleotide sequences of SEQ ID NOs: 17 and 18, a primer set of nucleotide sequences of SEQ ID NOs: 19 and 20, a primer set of nucleotide sequences of SEQ ID NOs: 21 and 22, a primer set of nucleotide sequences of SEQ ID NOs: 23 and 24, a primer set of nucleotide sequences of SEQ ID NOs: 25 and 26, or a primer set of nucleotide sequences of SEQ ID NOs: 27 and 28, thereby amplifying and obtaining genes of SEQ ID NOs: 8 to 14.

TABLE 1

| Number | | Forward primer sequence | Reverse primer sequence |
|---|---|---|---|
| 1 | T2 | SEQ ID NO: 15 | SEQ ID NO: 16 |
| 2 | T4 | SEQ ID NO: 17 | SEQ ID NO: 18 |
| 3 | T5 | SEQ ID NO: 19 | SEQ ID NO: 20 |
| 4 | T6 | SEQ ID NO: 21 | SEQ ID NO: 22 |
| 5 | T8 | SEQ ID NO: 23 | SEQ ID NO: 24 |
| 6 | T9 | SEQ ID NO: 25 | SEQ ID NO: 26 |
| 7 | T10 | SEQ ID NO: 27 | SEQ ID NO: 28 |

The amplified gene of SEQ ID NO: 8 (T2), the amplified gene of SEQ ID NO: 9 (T4), the amplified gene of SEQ ID NO: 10 (T5), the amplified gene of SEQ ID NO: 11 (T6), the amplified gene of SEQ ID NO: 12 (T8), the amplified gene of SEQ ID NO: 13 (T9), and the amplified gene of SEQ ID NO: 14 (T10) were each ligated into pET28a vectors (Novagen, Cat. No. 69864-3), which had been digested with NcoI and XhoI restriction enzymes, using an InFusion Cloning Kit (Clontech Laboratories, Inc.) to prepare pET28a-PE vectors for expressing T2, T4, T5, T6, T8, T9, and T10 genes, respectively. The expressed genes were each then named pT4, pT5, pT6, pT8, pT9, and pT10.

FIG. 1 shows a vector map of pET28a-PE (pT2, pT4, pT5, pT6, pT8, pT9, and pT10) into which an exogenous gene was introduced. Referring to FIG. 1, the exogenous gene (T2, T4, T5, T6, T8, T9, or T10) may be a gene of SEQ ID NOs: 8 to 14.

Next, each of the prepared pT2, pT4, pT5, pT6, pT8, pT9, and pT10 vectors was introduced to an *E. coli* BL21 strain by a heat shock method (Sambrook, J & Russell, D. W., New York: Cold Spring Harbor Laboratory Press, 2001), and then the strains were cultured on an LB plate containing kanamycin (50 µg/mL). A strain showing kanamycin resistance was screened and selected from the cultured strains. Finally, the selected strain was then designated as a recombinant *E. coli* BL21/pT2, a recombinant *E. coli* BL21/pT4, a recombinant *E. coli* BL21/pT5, a recombinant *E. coli* BL21/pT6, a recombinant *E. coli* BL21/pT8, a recombinant *E. coli* BL21/pT9, and a recombinant *E. coli* BL21/pT10.

(2) Evaluation of Effect of a Recombinant *E. coli* Expressing Polypeptides of SEQ ID NOs: 1 to 7 on Degradation of a Macromolecular Substance Effects of the *E. coli* BL21/pT2, BL21/pT4, BL21/pT5, BL21/pT6, BL21/pT8, BL21/pT9, and BL21/pT10 strains into which each of SEQ ID NOs: 8 to 14 was introduced prepared in Example 1(1) were examined in relation to degradation of a macromolecular substance.

Each of the *E. coli* BL21/pT2, BL21/pT4, BL21/pT5, BL21/pT6, BL21/pT8, BL21/pT9, and BL21/pT10 strains were cultured in a TB medium at a temperature of 30° C. while being stirred at 230 rpm. At $OD_{600}$ of about 0.5, 0.2 mM of IPTG was added thereto, followed by culturing at a temperature of 20° C. while being stirred at 230 rpm overnight.

Cells were harvested from the culture by centrifugation. The BugBuster protein extraction reagent (Novagen) was used to disrupt the cell walls of *E. coli*, thereby obtaining crude extracts of *E. coli*. Amino acid sequences of proteins in the crude extracts are shown in Table 2. The total protein concentration in the crude extracts was quantified by a Bradford method. The total protein concentration in the crude extracts and the amount of protein used in degradation of polyethylene are shown in Table 3

TABLE 2

| Number | | Amino acid sequence |
|---|---|---|
| 1 | T2 | SEQ ID NO: 1 |
| 2 | T4 | SEQ ID NO: 2 |
| 3 | T5 | SEQ ID NO: 3 |
| 4 | T6 | SEQ ID NO: 4 |
| 5 | T8 | SEQ ID NO: 5 |
| 6 | T9 | SEQ ID NO: 6 |
| 7 | T10 | SEQ ID NO: 7 |

TABLE 3

| Number | | Total protein concentration (mg/mL) | Amount of protein used in degradation of polyethylene (mg) |
|---|---|---|---|
| 1 | T2 | 31.4 | 62.8 |
| 2 | T4 | 35.5 | 106.7 |
| 3 | T5 | 13.9 | 27.8 |
| 4 | T6 | 38.9 | 77.9 |
| 5 | T8 | 24.4 | 73.2 |
| 6 | T9 | 11.0 | 22.0 |
| 7 | T10 | 10.0 | 20.0 |

(3) Measurement of Changes in Tensile Strength of a Macromolecular Substance 3 pieces of a polyethylene film having a weight average molecular weight of about 155,000, determined by Gel permeation chromatography (GPC), width×height of 1 cm×5 cm, and a mass of about 30 mg; and 10 mL of phosphate buffer saline (PBS) having a pH of 7.4 and containing 62.8 mg of crude extractions of T2 protein obtained from Example 1(2) were added to a 15 mL tube. The contents of the tube were reacted while being stirred at a temperature of 30° C. at 120 rpm for 7 days. Such a process was repeated in triplicate. As a control group, a crude extract obtained by introducing an empty pET28a vector to an *E. coli* BL21 strain by a heat shock method and culturing the recombinant microorganism was used. For each of T4, T5, T8, T9, and T10 protein, the same procedure was used except that an amount of protein shown in Table 3 was used. After the reaction, the polyethylene film pieces were washed with a 2% sodium dodecyl sulfate (SDS) solution for 4 hours, cleaned with deionized water, and dried at room temperature overnight.

The dried polyethylene film pieces were subjected to a texture analyzer (TA.XT plus, Stable Micro Systems) so that these samples were each pulled at 5 mm/min to calculate tensile strength, which is stress at the time of fracture. Table 4 shows changes in tensile strength of the polyethylene after reacting the polyethylene with a recombinant protein of T2, T4, T5, T8, T9, T10, and the control group.

TABLE 4

| Number | Sample | Tensile strength (MPa) | Tensile strength (%) |
| --- | --- | --- | --- |
| 1 | Control group | 11.52 | 100 |
| 2 | T2 | 8.36 | 72.57 |
| 3 | T4 | 10.19 | 88.42 |
| 4 | T5 | 10.10 | 87.65 |
| 5 | T8 | 9.54 | 82.79 |
| 6 | T9 | 9.23 | 80.12 |
| 7 | T10 | 9.04 | 78.50 |

As shown in Table 4, each of the crude extracts containing a recombinant protein of T2, T4, T5, T8, T9, or T10 shows significantly reduced tensile strength of polyethylene relative to that of the control group.

(4) Infrared Spectroscopy Change Measurement

Whether a C—H bond or C—C bond of polyethylene was converted into a C=O bond was confirmed by using a Fourier transform infrared spectrometer (FTIR) (Varian 670 IR, Agilent, Calif., USA). Spectroscopic analysis was carried out using a Miracle™ accessory manufactured by Pike Company (PA, USA) with an Attenuated Total Reflection Mode (ATR). For the total reflection of light, germanium crystals having an index of refraction of 4 were used. A mercury cadmium telluride (MCT, HgCdTe) detector including liquid nitrogen was used to measure light absorption properties of polyethylene at room temperature. At a measurement range of about 4,000 to about 650 $cm^{-1}$, scanning was performed 64 times to obtain an absorption spectrum of an organic substance (polyethylene) against infrared rays.

Figure 3:
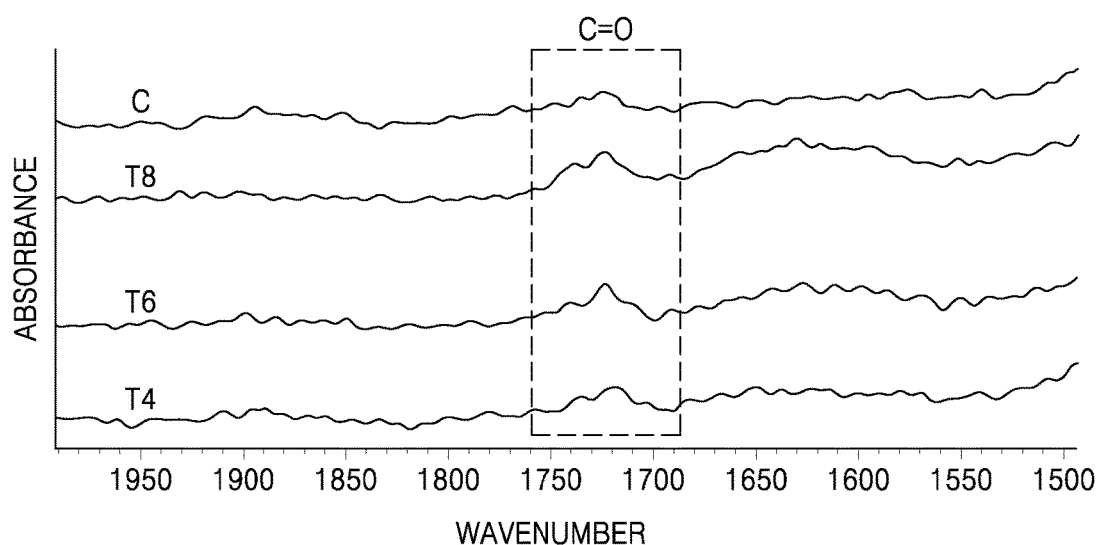
FIG. 3 shows a graph of experimental data showing that crude extracts containing T4, T6, and T8 proteins increase C=O bonds of polyethylene compared to control proteins.

FIG. 3 shows a graph confirming that crude extracts containing T4, T6, and T8 proteins, respectively, increased C=O bonds in the polyethylene compared to control proteins.

Figure 4:
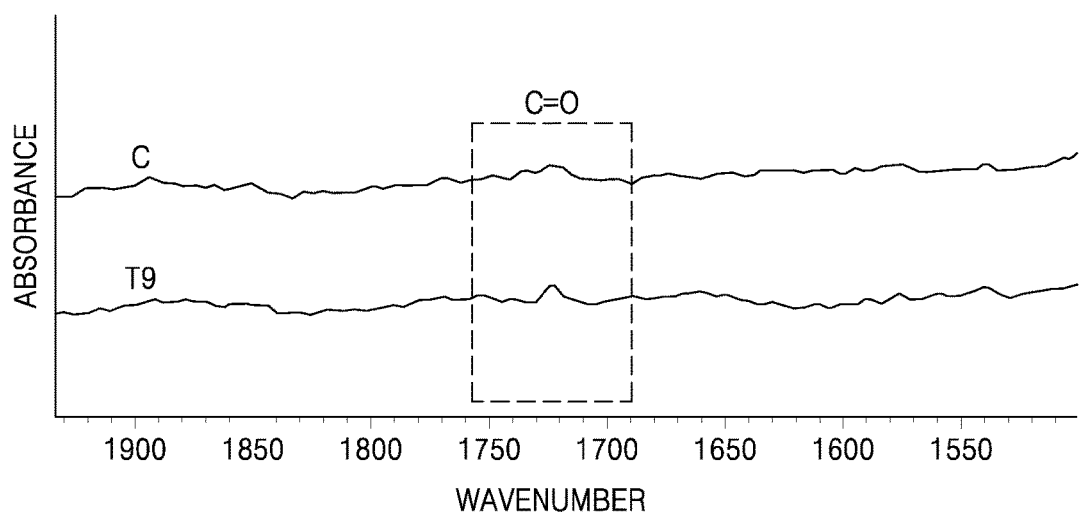
FIG. 4 shows a graph of experimental data showing that crude extracts containing T9 protein increase C=O bonds of polyethylene compared to control proteins.

FIG. 4 shows a graph confirming that crude extracts containing T9 increase C=O bonds of the polyethylene compared to control. Specifically, the crude extract containing T2, T4, T5, T8, T9, or T10 proteins showed clear s, relative to the control group, in the spectrum at around 1,725 $cm^{-1}$, thereby confirming the increase in C=O bonds.

Table 5 shows a peak ratio confirming that crude extracts containing T2, T4, T5, T6, T8, and T9, respectively, increase C=O bonds of the polyethylene compared to control. crude extracts containing T2, T4, T5, T6, T8, and T9, respectively, increased the C=O/C—H ratio by about 2.0 to about 2.7 fold.

TABLE 5

| | Peak ratio (C=O/C—H) |
| --- | --- |
| Control | 0.0004 |
| T2 | 0.0018 |
| T4 | 0.0022 |
| T5 | 0.0008 |
| T6 | 0.0028 |
| T8 | 0.0029 |
| T9 | 0.0008 |

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of degrading a polyalkylene compound, the method comprising:

contacting the polyalkylene compound with a recombinant microorganism, a lysate thereof, or a fraction of the lysate thereof, wherein the recombinant microorganism expresses a recombinant protein comprising the amino acid sequence of SEQ ID NO:1, and wherein the polyalkylene compound has an alkylene repeat unit of 1 to 10 carbon atoms.

2. The method of claim 1, wherein the contacting is performed in a sealed container.

3. The method of claim 1, wherein the recombinant microorganism expresses the recombinant protein at an increased level relative to a parent strain.

4. The method of claim 1, wherein the recombinant protein catalyzes oxidation or conversion of a carbon-hydrogen or carbon-carbon bond to a carbon-oxygen bond in the polyalkylene compound.

5. The method of claim 1, wherein the recombinant microorganism comprises an increased copy number of a gene that encodes the recombinant protein relative to a parent strain.

6. The method of claim 5, wherein the gene comprises the nucleotide sequence of SEQ ID NO:8.

7. The method of claim 1, wherein the recombinant microorganism belongs to the genus *Escherichia*, the genus *Xanthomonas*, genus *Xanthobacter*, the genus *Salmonella*, the genus *Pseudomonas*, the genus *Corynebacterium*, the genus *Bacillus*, or the genus *Saccharomyces*.

8. The method of claim 1, wherein the polyalkylene compound is polyethylene.

* * * * *

SEQUENCE LISTING

<160> NUMBER OF SEQ ID NOS: 28

<210> SEQ ID NO 1

```
<211> LENGTH: 483
<212> TYPE: PRT
<213> ORGANISM: Bacillus subtilis
<220> FEATURE:
<221> NAME/KEY: misc_feature
<222> LOCATION: (1)..(483)
<223> OTHER INFORMATION: Bacillus sp. YP1

<400> SEQUENCE: 1
```

Met Gly Ile Ile Asn Gly Lys Glu Phe Ile Asp Arg Leu Asn Lys Leu
1               5                   10                  15

Glu Asn Glu Ile Trp Tyr Asp Gly Glu Lys Ile Lys Gly Asn Ile Ser
            20                  25                  30

Glu His Pro Ala Phe Lys Gly Ile Ile Lys Thr Lys Ser Ser Leu Tyr
        35                  40                  45

Glu Leu Gln Thr Lys Asp Glu Leu Ile His Glu Met Thr Tyr Cys Leu
    50                  55                  60

Pro Gly Asp His Asn Arg Ile Gly Leu Ser Tyr Leu Gln Pro Lys Thr
65                  70                  75                  80

Lys Asn Asp Leu Lys Lys Arg Arg Thr Met Ile Glu His Trp Ala Arg
                85                  90                  95

His Thr His Gly Met Met Gly Arg Ser Pro Asp Tyr Met Asn Thr Val
            100                 105                 110

Met Met Ser Phe Ala Ser Ser Ala Glu Leu Leu Lys Asp Lys Glu Asn
        115                 120                 125

Cys Phe Pro Glu His Ile Leu Asp Met Tyr Glu Gln Ala Ala Lys His
    130                 135                 140

Asp Leu Ser Phe Thr His Thr Phe Ile Thr Pro Gln Val Asn Arg Ser
145                 150                 155                 160

Gln Ser Tyr Phe Gly Leu Ser Glu Lys Pro Ile Ser Ala Lys Val Ile
                165                 170                 175

Asp Arg Thr Glu Lys Gly Leu Met Ile His Gly Ala Arg Leu Leu Ala
            180                 185                 190

Thr Gln Gly Gly Leu Thr Asp Glu Ile Leu Val Phe Ser Ala Pro Lys
        195                 200                 205

Phe Phe Phe Glu Thr Asp Glu Ala Tyr Ala Phe Ser Ile Pro Ser Asn
    210                 215                 220

Thr Lys Gly Val Lys Phe Ile Thr Arg Glu Ser Phe Val Leu Ser Asp
225                 230                 235                 240

Ser Ser Phe Asn His Pro Leu Ser Ser Arg Tyr Glu Glu Met Asp Ser
                245                 250                 255

Ile Val Val Phe Asp His Val Leu Val Pro Trp Asn Arg Val Phe Phe
            260                 265                 270

Tyr Asp Asn Val Glu Ala Ala Lys Asp Phe Met Thr Lys Ser Ser Phe
        275                 280                 285

His Ala Phe Thr Phe His Gln Val Val Ile Arg Gln Met Ile Lys Ile
    290                 295                 300

Glu Phe Leu Leu Gly Val Ala Gln Leu Leu Val Asp Thr Ile Asn Val
305                 310                 315                 320

Ser Glu Tyr Gln His Ile Gln Glu Lys Leu Ser Glu Ile Ile Val Gly
                325                 330                 335

Leu Glu Thr Ile Lys Ala Leu Ile Asp Lys Ser Glu Asn Asp Ala Gln
            340                 345                 350

Leu Asp Glu Phe Gly Tyr Met Arg Pro Cys Leu Ile Pro Leu Gln Val
        355                 360                 365

```
Ile Ser Thr Ile Ile Pro Lys Leu Tyr Pro Arg Phe Thr Glu Ile Ile
        370                 375                 380

Gln Leu Ile Gly Ala Ser Gly Met Val Thr Leu Pro Thr Glu Asn Ala
385                 390                 395                 400

Phe Asp Ser Glu Ile Arg Glu Asp Leu Asp Gln Tyr Leu Gln Ala Thr
                405                 410                 415

Asn Thr Asn Ala Glu Glu Arg Val Lys Ile Phe Arg Leu Ala Trp Asp
            420                 425                 430

Leu Thr Met Ser Ser Phe Gly Thr Arg Gln Thr His Tyr Glu Arg Tyr
        435                 440                 445

Phe Phe Gly Asp Pro Ile Arg Ile Ser Ser Arg Leu Tyr Thr Ser Tyr
450                 455                 460

Pro Lys Gln Glu Gln Leu Asn Met Ile Lys Thr Phe Leu His Ala Asp
465                 470                 475                 480

Ala Glu Gln

<210> SEQ ID NO 2
<211> LENGTH: 442
<212> TYPE: PRT
<213> ORGANISM: Bacillus subtilis
<220> FEATURE:
<221> NAME/KEY: misc_feature
<222> LOCATION: (1)..(442)
<223> OTHER INFORMATION: Bacillus sp. YP1

<400> SEQUENCE: 2

Met Thr Arg Ser Asp Phe Ile Gln Phe Gly Ala Met Ile His Gly Val
1               5                   10                  15

Gly Gly Thr Thr Asp Gly Trp Arg His Pro Asp Val Asp Pro Ser Ala
            20                  25                  30

Ser Thr Asn Ile Glu Phe Tyr Met Lys Lys Ala Gln Thr Ala Glu Lys
        35                  40                  45

Gly Leu Phe Ser Phe Ile Phe Ile Ala Asp Gly Leu Phe Ile Ser Glu
    50                  55                  60

Lys Ser Ile Pro His Phe Leu Asn Arg Phe Glu Pro Ile Thr Ile Leu
65                  70                  75                  80

Ser Ala Leu Ala Ser Val Thr Lys Asn Ile Gly Leu Val Gly Thr Phe
                85                  90                  95

Ser Thr Ser Phe Thr Glu Pro Phe Thr Ile Ser Arg Gln Leu Met Ser
            100                 105                 110

Leu Asp His Ile Ser Gly Gly Arg Ala Gly Trp Asn Leu Val Thr Ser
        115                 120                 125

Pro Gln Glu Gly Ala Ala Arg Asn His Ser Lys Ser Asn Leu Pro Glu
130                 135                 140

His Thr Glu Arg Tyr Glu Ile Ala Gln Glu His Leu Asp Val Val Arg
145                 150                 155                 160

Gly Leu Trp Asn Ser Trp Glu His Asp Ala Phe Ile His Asn Lys Lys
                165                 170                 175

Thr Gly Gln Phe Phe Asp Pro Ala Lys Leu His Arg Leu Asn His Lys
            180                 185                 190

Gly Lys Tyr Phe Gln Val Glu Gly Pro Leu Asn Ile Gly Arg Ser Lys
        195                 200                 205

Gln Gly Glu Pro Val Val Phe Gln Ala Gly Ser Ser Glu Thr Gly Arg
    210                 215                 220

Gln Phe Ala Ala Lys Asn Ala Asp Ala Ile Phe Thr His Ser Asn Ser
225                 230                 235                 240
```

```
Leu Glu Glu Thr Lys Ala Phe Tyr Ala Asp Val Lys Arg Arg Ala Ala
                245                 250                 255

Asp Lys Gly Arg Asp Pro Ser Ser Val Arg Ile Phe Pro Gly Ile Ser
            260                 265                 270

Pro Ile Val Ala Asp Thr Glu Glu Ala Glu Lys Lys Tyr Arg Glu
            275                 280                 285

Phe Ala Glu Leu Ile Pro Ile Glu Asn Ala Val Thr Tyr Leu Ala Arg
            290                 295                 300

Phe Phe Asp Asp Tyr Asp Leu Ser Val Tyr Pro Leu Asp Glu Pro Phe
305                 310                 315                 320

Pro Asp Ile Gly Asp Val Gly Lys Asn Ala Phe Gln Ser Thr Thr Asp
                325                 330                 335

Arg Ile Lys Arg Glu Ala Lys Ala Arg Asn Leu Thr Leu Arg Glu Val
                340                 345                 350

Ala Gln Glu Met Ala Phe Pro Arg Pro Leu Phe Ile Gly Thr Pro Glu
                355                 360                 365

Arg Val Ala Ser Leu Ile Glu Thr Trp Phe Asn Ala Glu Ala Ala Asp
                370                 375                 380

Gly Phe Ile Ile Gly Ser Asp Ile Pro Gly Thr Leu Asp Ala Phe Val
385                 390                 395                 400

Glu Lys Val Ile Pro Ile Leu Gln Glu Arg Gly Leu Tyr Arg Gln Asp
                405                 410                 415

Tyr Arg Gly Gly Thr Leu Arg Glu Asn Leu Gly Leu Gly Ile Pro Gln
                420                 425                 430

His Gln Ser Val Leu His Ser Ser His His
                435                 440

<210> SEQ ID NO 3
<211> LENGTH: 432
<212> TYPE: PRT
<213> ORGANISM: Bacillus subtilis
<220> FEATURE:
<221> NAME/KEY: misc_feature
<222> LOCATION: (1)..(432)
<223> OTHER INFORMATION: Bacillus sp. YP1

<400> SEQUENCE: 3

Met Leu Phe Lys Lys Asp Arg Lys Gln Glu Thr Ala Tyr Phe Ser Asp
1               5                   10                  15

Ser Asn Gly Gln Gln Lys Asn Arg Ile Gln Leu Thr Asn Lys His Ala
                20                  25                  30

Asp Val Lys Lys Gln Leu Lys Met Val Arg Leu Gly Asp Ala Glu Leu
            35                  40                  45

Tyr Val Leu Glu Gln Leu Gln Pro Leu Ile Gln Glu Asn Ile Val Asn
        50                  55                  60

Ile Val Asp Ala Phe Tyr Lys Asn Leu Asp His Glu Ser Ser Leu Met
65                  70                  75                  80

Asp Ile Ile Asn Asp His Ser Ser Val Asp Arg Leu Lys Gln Thr Leu
                85                  90                  95

Lys Arg His Ile Gln Glu Met Phe Ala Gly Val Ile Asp Asp Glu Phe
            100                 105                 110

Ile Glu Lys Arg Asn Arg Ile Ala Ser Ile His Leu Arg Ile Gly Leu
        115                 120                 125

Leu Pro Lys Trp Tyr Met Gly Ala Phe Gln Glu Leu Leu Leu Ser Met
    130                 135                 140
```

```
Ile Asp Ile Tyr Glu Ala Ser Ile Thr Asn Gln Gln Glu Leu Leu Lys
145                 150                 155                 160

Ala Ile Lys Ala Thr Thr Lys Ile Leu Asn Leu Glu Gln Gln Leu Val
            165                 170                 175

Leu Glu Ala Phe Gln Ser Glu Tyr Asn Gln Thr Arg Asp Glu Gln Glu
        180                 185                 190

Glu Lys Lys Asn Leu Leu His Gln Lys Ile Gln Glu Thr Ser Gly Ser
    195                 200                 205

Ile Ala Asn Leu Phe Ser Glu Thr Ser Arg Ser Val Gln Glu Leu Val
210                 215                 220

Asp Lys Ser Glu Gly Ile Ser Gln Ala Ser Lys Ala Gly Thr Val Thr
225                 230                 235                 240

Ser Ser Thr Val Glu Glu Lys Ser Ile Gly Gly Lys Lys Glu Leu Glu
            245                 250                 255

Val Gln Gln Lys Gln Met Asn Lys Ile Asp Thr Ser Leu Val Gln Ile
        260                 265                 270

Glu Lys Glu Met Val Lys Leu Asp Glu Ile Ala Gln Gln Ile Glu Lys
    275                 280                 285

Ile Phe Gly Ile Val Thr Gly Ile Ala Glu Gln Thr Asn Leu Leu Ser
290                 295                 300

Leu Asn Ala Ser Ile Glu Ser Ala Arg Ala Gly Glu His Gly Lys Gly
305                 310                 315                 320

Phe Ala Val Val Ala Asn Glu Val Arg Lys Leu Ser Glu Asp Thr Lys
            325                 330                 335

Lys Thr Val Ser Thr Val Ser Glu Leu Val Asn Asn Thr Asn Thr Gln
        340                 345                 350

Ile Asn Ile Val Ser Lys His Ile Lys Asp Val Asn Glu Leu Val Ser
    355                 360                 365

Glu Ser Lys Glu Lys Met Thr Gln Ile Asn Arg Leu Phe Asp Glu Ile
370                 375                 380

Val His Ser Met Lys Ile Ser Lys Glu Gln Ser Gly Lys Ile Asp Val
385                 390                 395                 400

Asp Leu Gln Ala Phe Leu Gly Gly Leu Gln Glu Val Ser Arg Ala Val
            405                 410                 415

Ser His Val Ala Ala Ser Val Asp Ser Leu Val Ile Leu Thr Glu Glu
        420                 425                 430

<210> SEQ ID NO 4
<211> LENGTH: 347
<212> TYPE: PRT
<213> ORGANISM: Bacillus subtilis
<220> FEATURE:
<221> NAME/KEY: misc_feature
<222> LOCATION: (1)..(347)
<223> OTHER INFORMATION: Bacillus sp. YP1

<400> SEQUENCE: 4

Met Asn Glu Phe Met Lys Lys Phe Ser Leu Thr Lys Pro Ile Ile Gln
1               5                   10                  15

Ala Pro Met Ala Gly Gly Ile Thr Thr Pro Arg Leu Ala Ser Ala Val
            20                  25                  30

Ser Asn Gln Gly Ala Leu Gly Ser Leu Ala Ser Gly Tyr Leu Thr Pro
        35                  40                  45

Asp Leu Leu Glu Gln Gln Ile Lys Glu Met Phe Glu Leu Thr Asp Ala
    50                  55                  60

Pro Phe Gln Ile Asn Val Phe Val Pro Leu Gly Leu Glu Met Pro Pro
```

```
            65                  70                  75                  80
        Glu Asp Gln Ile Lys Lys Trp Lys Glu Asn Ile Pro Leu Ala Asn Gln
                        85                  90                  95
        Val Asn Gln Phe Thr Ser Val Gln Glu Glu Trp Asp Phe Tyr Gln
                        100                 105                 110
        Lys Ile Asp Leu Ile Leu Lys Tyr Lys Val Lys Ala Cys Ser Phe Thr
                        115                 120                 125
        Phe Asp Leu Pro Pro Glu Asp Ala Val Lys Glu Leu Lys Thr Ala Gly
                        130                 135                 140
        Cys Cys Leu Ile Gly Thr Ala Ser Thr Val Glu Glu Ala Leu Leu Met
        145                 150                 155                 160
        Glu Glu Arg Gly Met Asp Ile Val Val Leu Gln Gly Ser Glu Ala Gly
                            165                 170                 175
        Gly His Arg Gly Ala Phe Leu Pro Ser Lys Gly Glu Ser Ala Val Gly
                            180                 185                 190
        Leu Met Ala Leu Ile Pro Gln Ala Ala Asp Ala Leu Ser Val Pro Val
                        195                 200                 205
        Ile Ala Ala Gly Gly Met Ile Asp His Arg Gly Val Lys Ala Ala Leu
                210                 215                 220
        Thr Leu Gly Ala Gln Gly Val Gln Ile Gly Ser Ala Phe Leu Ile Cys
        225                 230                 235                 240
        His Glu Ser Asn Ala His Pro Val His Lys Gln Lys Ile Leu Glu Ala
                        245                 250                 255
        Asn Glu Ala Asp Thr Lys Leu Thr Thr Leu Phe Ser Gly Lys Glu Ala
                        260                 265                 270
        Arg Gly Ile Val Asn Lys Trp Met Glu Glu Lys Glu Gln Phe Glu Thr
                    275                 280                 285
        Gln Thr Leu Pro Tyr Pro Tyr Gln Asn Thr Leu Thr Lys Ala Met Arg
                        290                 295                 300
        Gln Lys Ala Ser Leu Gln Asn Asn His Asp Gln Met Ser Leu Trp Ala
        305                 310                 315                 320
        Gly Gln Gly Ile Arg Ser Leu Thr Glu Glu Ile Ser Val Lys Gln Leu
                        325                 330                 335
        Leu Asn Gln Leu Cys Gln Glu Asp Ile Lys Ile
                        340                 345

<210> SEQ ID NO 5
<211> LENGTH: 447
<212> TYPE: PRT
<213> ORGANISM: Bacillus subtilis
<220> FEATURE:
<221> NAME/KEY: misc_feature
<222> LOCATION: (1)..(447)
<223> OTHER INFORMATION: Bacillus sp. YP1

<400> SEQUENCE: 5

Met Lys Asn Asp Asn Gln Thr Leu Lys Arg Thr Met Thr Ser Arg His
        1                   5                   10                  15
        Ile Met Met Met Ala Leu Gly Gly Ala Ile Gly Ala Gly Leu Phe Lys
                        20                  25                  30
        Gly Ser Ser Ala Ile Asp Val Ala Gly Pro Ser Val Ile Ile Ala
                    35                  40                  45
        Tyr Leu Leu Gly Gly Ile Ile Leu Phe Ile Met Gln Gly Leu Ala
                50                  55                  60
        Glu Met Ala Val Arg Asn Arg Asn Ala Arg Thr Phe Arg Asp Leu Val
        65                  70                  75                  80
```

-continued

```
Gln Gln Val Leu Gly Asn Tyr Ala Ala Tyr Phe Leu Asp Trp Ile Tyr
                85                  90                  95
Trp Lys Met Trp Val Leu Asn Ile Ala Ala Glu Ala Val Val Ala Ala
            100                 105                 110
Ile Phe Ile Gln Tyr Trp Leu Pro Gly Cys Pro Ile Trp Val Leu Ala
        115                 120                 125
Leu Gly Ile Ser Leu Ile Val Thr Ile Val Asn Leu Leu Ser Val Lys
    130                 135                 140
Ile Phe Ala Glu Thr Glu Tyr Trp Leu Ala Met Ile Lys Ile Thr Val
145                 150                 155                 160
Ile Ile Ile Phe Ile Ile Leu Gly Leu Leu Leu Phe Val Ser Phe
                165                 170                 175
Gly Asp His Thr Ala Ser Arg Phe Ser Asn Leu Thr Asp His Gly Gly
            180                 185                 190
Phe Phe Pro His Gly Gly Thr Gly Leu Ile Thr Ala Met Leu Val Val
        195                 200                 205
Ile Tyr Ser Tyr Gly Gly Thr Glu Ile Ile Gly Val Thr Leu Ala Glu
    210                 215                 220
Thr Lys Asn Pro Glu Lys Val Pro Lys Ala Val Arg Ser Thr Leu
225                 230                 235                 240
Thr Arg Ile Val Ala Phe Tyr Leu Leu Pro Phe Phe Ile Ile Val Ser
                245                 250                 255
Leu Ile Pro Trp Asn Gln Val Asn Ser Val Pro Glu Ser Pro Phe Val
            260                 265                 270
Met Val Phe Lys Met Val Gly Ile Pro Gly Ala Asp His Ile Met Asn
        275                 280                 285
Ala Val Ile Leu Leu Ala Ile Ile Ser Ser Met Asn Ser Gly Leu Tyr
    290                 295                 300
Gly Ser Ser Arg Ile Leu Tyr Thr Gln Ala Ser Asp Gly Arg Leu Pro
305                 310                 315                 320
Lys Val Phe Ser Lys Leu Ser Ser Lys Asn Val Pro Met Phe Ala Ile
                325                 330                 335
Leu Met Cys Thr Ser Ser Leu Tyr Ile Gly Val Leu Ile Ser Leu Phe
            340                 345                 350
Ala Gly Ser Gln Thr Phe Asn Tyr Leu Met Gly Ser Leu Gly Tyr Thr
        355                 360                 365
Val Leu Phe Ile Trp Leu Ile Ile Gly Phe Ala His Leu Lys Ser Arg
    370                 375                 380
Lys Gln Gln Thr Glu Thr Pro Ala Tyr Tyr Val Lys Trp Phe Pro Tyr
385                 390                 395                 400
Thr Thr Trp Phe Ala Ile Val Ala Leu Leu Ala Ile Leu Ile Gly Val
                405                 410                 415
Ile Met Thr Thr Ser Ile Val Ile Thr Gly Ile Thr Ala Ala Ile Tyr
            420                 425                 430
Leu Leu Ile Thr Val Ala Tyr Leu Val Lys Gly Arg Lys His Gln
        435                 440                 445
```

<210> SEQ ID NO 6
<211> LENGTH: 380
<212> TYPE: PRT
<213> ORGANISM: Bacillus subtilis
<220> FEATURE:
<221> NAME/KEY: misc_feature
<222> LOCATION: (1)..(380)
<223> OTHER INFORMATION: Bacillus sp. YP1

<400> SEQUENCE: 6

```
Met Lys Lys Glu Leu Ser Phe His Glu Lys Leu Leu Lys Leu Thr Lys
1               5                   10                  15
Gln Gln Lys Lys Lys Thr Asn Lys His Val Phe Ile Ala Ile Pro Ile
            20                  25                  30
Val Phe Val Leu Met Phe Ala Phe Met Trp Ala Gly Lys Ala Glu Thr
        35                  40                  45
Pro Lys Val Lys Thr Tyr Ser Asp Asp Val Leu Ser Ala Ser Phe Val
    50                  55                  60
Gly Asp Ile Met Met Gly Arg Tyr Val Glu Lys Val Thr Glu Gln Lys
65                  70                  75                  80
Gly Ala Asp Ser Ile Phe Gln Tyr Val Glu Pro Ile Phe Arg Ala Ser
                85                  90                  95
Asp Tyr Val Ala Gly Asn Phe Glu Asn Pro Val Thr Tyr Gln Lys Asn
            100                 105                 110
Tyr Lys Gln Ala Asp Lys Lys Ile His Leu Gln Thr Asn Lys Glu Ser
        115                 120                 125
Val Lys Val Leu Lys Asp Met Asn Phe Thr Val Leu Asn Ser Ala Asn
    130                 135                 140
Asn His Ala Met Asp Tyr Gly Val Gln Gly Met Lys Asp Thr Leu Gly
145                 150                 155                 160
Glu Phe Ala Lys Gln Asn Leu Asp Ile Val Gly Ala Gly Tyr Ser Leu
                165                 170                 175
Ser Asp Ala Lys Lys Lys Ile Ser Tyr Gln Lys Val Asn Gly Val Thr
            180                 185                 190
Ile Ala Thr Leu Gly Phe Thr Asp Val Ser Gly Lys Gly Phe Ala Ala
        195                 200                 205
Lys Lys Asn Thr Pro Gly Val Leu Pro Ala Asp Pro Glu Ile Phe Ile
    210                 215                 220
Pro Met Ile Ser Glu Ala Lys Lys His Ala Asp Ile Val Val Val Gln
225                 230                 235                 240
Ser His Trp Gly Gln Glu Tyr Asp Asn Asp Pro Asn Asp Arg Gln Arg
                245                 250                 255
Gln Leu Ala Arg Ala Met Ser Asp Ala Gly Ala Asp Ile Ile Val Gly
            260                 265                 270
His His Pro His Val Leu Glu Pro Ile Glu Val Tyr Asn Gly Thr Val
        275                 280                 285
Ile Phe Tyr Ser Leu Gly Asn Phe Val Phe Asp Gln Gly Trp Thr Arg
    290                 295                 300
Thr Arg Asp Ser Ala Leu Val Gln Tyr His Leu Lys Lys Asn Gly Thr
305                 310                 315                 320
Gly Arg Phe Glu Val Thr Pro Ile Asp Ile His Glu Ala Thr Pro Ala
                325                 330                 335
Pro Val Lys Lys Asp Ser Leu Lys Gln Lys Thr Ile Ile Arg Glu Leu
            340                 345                 350
Thr Lys Asp Ser Asn Phe Ala Trp Lys Val Glu Asp Gly Lys Leu Thr
        355                 360                 365
Phe Asp Ile Asp His Ser Asp Lys Leu Lys Ser Lys
    370                 375                 380

<210> SEQ ID NO 7
<211> LENGTH: 95
<212> TYPE: PRT
```

```
<213> ORGANISM: Bacillus subtilis
<220> FEATURE:
<221> NAME/KEY: misc_feature
<222> LOCATION: (1)..(95)
<223> OTHER INFORMATION: Bacillus sp. YP1

<400> SEQUENCE: 7

Met Val Arg Glu Ala Ala Met Leu His Ile Lys Glu Gly Leu Glu Gln
 1               5                  10                  15

Glu Phe Glu Asp Ala Phe Arg Gln Ala Ala Pro Ile Ile Ser Gly Met
            20                  25                  30

Lys Gly Tyr Ile Thr His Ser Leu Ser Lys Cys Met Glu Glu Thr His
        35                  40                  45

Lys Tyr Leu Leu Leu Val Glu Trp Glu Thr Leu Glu Asn His Thr Glu
    50                  55                  60

Gly Phe Arg Gly Ser Ser Glu Tyr Gln Glu Trp Lys Ala Leu Leu His
65                  70                  75                  80

Arg Phe Tyr Thr Pro Phe Pro Thr Val Glu His Phe Gln Asp Val
                85                  90                  95

<210> SEQ ID NO 8
<211> LENGTH: 1452
<212> TYPE: DNA
<213> ORGANISM: Bacillus subtilis
<220> FEATURE:
<221> NAME/KEY: misc_feature
<222> LOCATION: (1)..(1452)
<223> OTHER INFORMATION: Bacillus sp. YP1

<400> SEQUENCE: 8
atgggtatca tcaacggtaa agagttcatc gaccgcctga caagctggaa gaatgagatc      60
tggtatgacg gcgagaagat caagggtaac atcagcgagc accctgcatt caaaggtatc     120
attaagacca agtccagcct gtacgagctg caaaccaaag acgagctgat ccacgaaatg     180
acgtactgcc tgcctggtga tcataatcgt atcggtctgt cctacctgca gccaaaaacg     240
aaaaacgacc tgaagaaacg ccgtactatg atcgagcact gggctcgtca tactcacggt     300
atgatgggtc gttctccaga ttacatgaac actgtcatga tgagcttcgc ttccagcgca     360
gaactgctga agataaaga aaactgcttc ccggaacaca tcctggacat gtacgaacag     420
gctgctaaac acgacctgtc cttcactcac actttcatca ccccacaggt aaaccgtagc     480
cagtcttact tcggcctgtc tgaaaaaccg atctccgcta agtaatcga tcgcactgaa     540 aagggtctga tgatccatgg cgcacgtctg ctggcaactc aaggtggtct gactgatgaa     600
attctggttt tcagcgcacc gaaattcttt tttgaaaccg acgaagctta cgctttctcc     660
atcccgtcta acactaaagg tgtgaaattc attacccgcg agagcttcgt gctgagcgac     720
tcttctttca accacccgct gtcttctcgt tacgaagaaa tggactctat cgtcgtcttc     780
gaccacgtac tggtaccgtg aaccgtgtt tcttctacg acaacgttga agcggcgaaa     840
gacttcatga ccaaaagctc cttccacgca ttcaccttcc atcaggttgt tatccgtcag     900
atgatcaaaa tcgaattcct gctgggcgtg gcccagctgc tggttgatac catcaacgtt     960
tctgaatacc agcacatcca ggaaaaactg tccgaaatta tcgtgggcct ggaaaccatc    1020
aaagccctga ttgacaaatc cgaaaacgac gcgcagctgg atgaattcgg ctacatgcgc    1080
ccgtgtctga ttccgctgca agttatctct acgatcattc cgaaactgta cccgcgtttt    1140
acggaaatta ttcagctgat tggcgcgagc ggcatggtga ccctgccgac cgaaaatgcg    1200
tttgactctg aaatccgtga agatctggat caatatctgc aggccaccaa caccaacgcg    1260
```
gaagaacgtg tgaaaatttt tcgtctggcc tgggatctga ccatgtcttc ttttggcacg      1320
cgtcagaccc attatgaacg ctattttttt ggcgatccga ttcgcatttc ctcccgcctg      1380
tatacctcct atccgaaaca ggaacagctg aacatgatta aaacctttct gcacgcggat      1440
gcggaacagt aa                                                         1452

<210> SEQ ID NO 9
<211> LENGTH: 1329
<212> TYPE: DNA
<213> ORGANISM: Bacillus subtilis
<220> FEATURE:
<221> NAME/KEY: misc_feature
<222> LOCATION: (1)..(1329)
<223> OTHER INFORMATION: Bacillus sp. YP1

<400> SEQUENCE: 9
atgacccgta gcgatttcat ccagttcggt gcaatgatcc acggtgtcgg tggcactact       60
gacggttggc gtcatcctga tgttgatcct tctgcatcta cgaacatcga attctacatg      120
aagaaggccc agaccgctga aagggtctg ttctccttca tcttcatcgc ggacggcctg       180
ttcatcagcg agaagtccat ccctcacttc ctgaaccgtt tcgagccaat caccatcctg      240
agcgcactgg catctgtcac taagaacatt ggtctggtcg gtacgttctc caccagcttc      300
accgagccat tcaccatctc ccgtcagctg atgtctctgg atcacatctc cggtggtcgt      360
gcaggttgga atctggttac gagcccacaa gaaggtgcag cacgtaatca cagcaaaagc      420
aacctgccgg aacacactga gcgttacgag atcgcacagg aacacctgga tgtggttcgt      480
ggtctgtgga actcttggga acacgatgct ttcattcaca caaaaaaaac cggtcagttc      540
ttcgacccgg cgaaactgca tcgcctgaac cacaaaggca atacttcca ggtggagggt      600 ccgctgaaca tcggccgctc taaacagggc gaaccggtgg tattccaggc tggttcttct      660
gaaaccggcc gtcaattcgc tgctaaaaac gcagacgcta tcttcaccca ctccaactcc      720
ctggaagaaa ccaaagcgtt ctacgcggac gtgaaacgcc gcgctgctga taaaggtcgt      780
gacccgtctt ctgtacgtat ttttccgggt atcagcccga tcgtagctga cacggaagag      840
gaggctgaaa aaaatacccg cgaatttgcc gaactgatcc cgatcgaaaa cgcggtgacc      900
tacctggccc gcttctttga cgactacgac ctgtccgtgt atccgctgga cgaaccgttc      960
ccggacatcg tgatgttgg caaaaatgcg tttcagagca ccaccgaccg tatcaaacgc      1020
gaagcgaaag cccgtaacct gactctgcgt gaagttgcgc aagaaatggc gtttccgcgt      1080
ccgctgttta tcggcactcc ggaacgtgtt gcctctctga ttgaaacttg gtttaacgcg      1140
gaagccgcgg atggctttat tattggctcc gacattccgg gcaccctgga tgcgtttgta      1200 gaaaagtta ttccgattct gcaggaacgt ggcctgtatc gtcaggatta tcgcggcggc      1260
actctgcgcg aaaacctggg cctgggcatt ccgcagcatc agtccgttct gcattctagc      1320
catcactaa                                                             1329

<210> SEQ ID NO 10
<211> LENGTH: 1299
<212> TYPE: DNA
<213> ORGANISM: Bacillus subtilis
<220> FEATURE:
<221> NAME/KEY: misc_feature
<222> LOCATION: (1)..(1299)
<223> OTHER INFORMATION: Bacillus sp. YP1

<400> SEQUENCE: 10

| | |
|---|---|
| atgctgttta agaaggaccg taagcaagag actgcttact ttagcgacag caacggtcag | 60 |
| caaaagaacc gtatccagct gactaacaaa cacgcagacg taaaaaaaca gctgaaaatg | 120 |
| gtgcgcctgg gtgatgctga gctgtacgta ctggagcaac tgcagccact gatccaggaa | 180 |
| aatatcgtaa acatcgtcga cgcattctac aaaaacctgg accacgagtc ttctctgatg | 240 |
| gacatcatca cgaccattc cagcgtcgat cgtctgaaac agacgctgaa acgtcatatc | 300 |
| caggagatgt tcgcaggtgt aatcgatgat gagttcattg agaaacgcaa ccgtattgcg | 360 |
| tctatccacc tgcgtatcgg tctgctgccg aaatggtata tgggtgcatt tcaagagctg | 420 |
| ctgctgtcta tgattgacat ctacgaggca tctatcacta accagcagga actgctgaaa | 480 |
| gcaatcaaag cgactactaa atcctgaac ctggaacagc agctggtcct ggaagctttc | 540 |
| cagtctgaat ataaccagac ccgtgacgaa caggaagaga agaagaacct gctgcaccag | 600 |
| aaaattcagg aaacctccgg ttctatcgct aacctgttct ctgaaacctc tcgttctgtg | 660 |
| caagaactgg tcgacaagtc tgaaggtatc tctcaggctt ctaaagctgg tactgtgacc | 720 |
| tcttccactg tggaagaaaa gtccatcggt ggcaaaaaag agctggaagt tcagcagaaa | 780 |
| cagatgaaca aaatcgacac cagcctggtt cagattgaaa agaaatggt gaaactggac | 840 |
| gaaatcgccc agcagatcga aaaaatcttc ggcatcgtga ccggcatcgc ggaacagacc | 900 |
| aatctgctgt ccctgaacgc ttccatcgaa agcgcccgtg ccggtgaaca tggcaaaggc | 960 |
| ttcgcggttg ttgcgaatga agttcgcaaa ctgagcgaag atacgaaaaa aaccgttttcc | 1020 |
| accgtttctg aactggttaa caacaccaac acgcaaatta atatcgtgtc caaacacatt | 1080 |
| aaagatgtga cgaactggt gagcgaatcc aaagaaaaaa tgacccagat taaccgcctg | 1140 |
| ttcgatgaaa ttgttcacag catgaaaatt agcaaagaac agagcggcaa aattgatgtt | 1200 |
| gatctgcagg cgttcctggg cggcctgcag gaagtaagcc gcgccgtttc ccacgttgcg | 1260 |
| gcgtccgttg attccctggt aattctgacc gaagaataa | 1299 |

```
<210> SEQ ID NO 11
<211> LENGTH: 1044
<212> TYPE: DNA
<213> ORGANISM: Bacillus subtilis
<220> FEATURE:
<221> NAME/KEY: misc_feature
<222> LOCATION: (1)..(1044)
<223> OTHER INFORMATION: Bacillus sp. YP1

<400> SEQUENCE: 11
```

| | |
|---|---|
| atgaacgagt tcatgaagaa gttcagcctg accaagccga tcatccaggc tccaatggct | 60 |
| ggcggtatca ccactcctcg tctggcatct gcagtttcta accagggtgc tctgggttct | 120 |
| ctggcttctg gttacctgac tccagatctg ctggaacaac agatcaagga gatgttcgag | 180 |
| ctgaccgatg caccatttca gattaacgtg ttcgtgccgc tgggtctgga gatgccgcct | 240 |
| gaagatcaaa tcaagaaatg gaagagaac atcccgctgg ctaaccaagt caaccagttc | 300 |
| acctccgtcc aggaagaatg ggacgacttc taccagaaaa tcgacctgat cctgaaatac | 360 |
| aaagtgaaag cttgcagctt caccttcgac ctgccgccgg aagacgccgt gaaagaactg | 420 |
| aaaaccgctg gttgctgtct gatcggcacc gctagcaccg tggaggaagc cctgctgatg | 480 |
| gaggaacgcg gtatggacat cgttgtactg cagggttctg aagcaggtgg tcaccgtggt | 540 |
| gcattcctgc cgtctaaagg tgaatctgct gttggtctga tggcactgat cccgcaagca | 600 |
| gccgatgcgc tgagcgttcc ggtaattgca gcgggcggca tgattgatca tcgtggcgtt | 660 |
| aaagcggcgc tgactctggg cgcgcagggc gttcagattg gctccgcctt tctgatttgt | 720 |

```
catgaatcca atgcgcaccc ggtacacaaa cagaaaattc tggaagcgaa tgaagcggat    780
actaaactga ctactctgtt tagcggcaaa gaagcccgtg gcattgtaaa caaatggatg    840
gaagaaaaag aacagtttga aacccagacc ctgccgtatc cgtatcagaa cacgctgacg    900
aaagcgatgc gccagaaagc gagcctgcag aacaaccacg accagatgtc cctgtgggcg    960
ggccagggca tccgttccct gacggaagaa atctccgtta acagctgct gaaccagctg    1020 tgccaagaag acatcaaaat ctaa                                            1044

<210> SEQ ID NO 12
<211> LENGTH: 1344
<212> TYPE: DNA
<213> ORGANISM: Bacillus subtilis
<220> FEATURE:
<221> NAME/KEY: misc_feature
<222> LOCATION: (1)..(1344)
<223> OTHER INFORMATION: Bacillus sp. YP1

<400> SEQUENCE: 12
atgaaaaacg acaaccagac gctgaagcgt acgatgacgt cccgtcacat tatgatgatg     60
gcgctgggtg gtgcaatcgg tgcaggtctg ttcaaaggtt cttcttccgc aatcgatgtg    120
gcaggtccat ctgtaatcat cgcatacctg ctgggcggta tcattctgct gttcatcatg    180
cagggtctgg cagaaatggc tgtccgtaac cgtaacgcac gtactttccg tgatctggtg    240
cagcaggtgc tgggtaacta tgctgcttac tttctggatt ggatctactg gaagatgtgg    300
gtcctgaaca tcgctgcgga agctgttgta gctgctatct tcattcagta ctggctgccg    360
ggttgtccta tttgggtact ggcactgggt attagcctga tcgttactat cgtgaacctg    420
ctgtctgtca agatcttcgc ggagactgag tattggctgg caatgatcaa atcaccgtc    480 atcattatct ttattatcct gggcctgctg ctgctgtttg tgagcttcgg cgaccacacc    540
gcgtcccgtt tctccaacct gactgaccac ggtggtttct ccctcacgg tggcaccggt    600 ctgattactg ccatgctggt agttatttac tcttacggcg gtactgaaat cattggcgtg    660
actctggctg aaactaaaaa cccggaaaaa gtcgttccga aagcggtgcg tagcactctg    720
acccgtatcg tggctttcta tctgctgccg ttcttcatca tcgtgtccct gatcccatgg    780
aatcaggtga acagcgttcc ggaatctccg tttgtaatgg ttttcaaaat ggtaggcatc    840
ccgggcgctg accatatcat gaacgccgtt atcctgctgg ctatcatcag cagcatgaac    900
tccggtctgt acggtagcag ccgcattctg tacacccaag cctctgatgg tcgcctgccg    960
aaagtttttt ctaaactgtc ttccaaaaat gtaccgatgt tcgccatcct gatgtgcacc    1020
tccagcctgt atatcggcgt actgatctcc ctgttcgcgg gctctcaaac cttcaattac    1080
ctgatgggct ccctgggcta taccgttctg ttcatttggc tgattatcgg cttcgcgcat    1140
ctgaaatctc gcaagcagca gaccgaaacc ccggcctatt atgttaaatg gtttccgtac    1200
accacctggt tgcgatcgt tgcgctgctg gccattctga ttggcgttat catgaccacc    1260
tctatcgtta tcacgggcat taccgcggcg atttacctgc tgattaccgt tgcgtacctg    1320
gttaaaggcc gcaaacacca gtaa                                           1344

<210> SEQ ID NO 13
<211> LENGTH: 1143
<212> TYPE: DNA
<213> ORGANISM: Bacillus subtilis
<220> FEATURE:
<221> NAME/KEY: misc_feature
<222> LOCATION: (1)..(1143)
```

<223> OTHER INFORMATION: Bacillus sp. YP1

<400> SEQUENCE: 13

| | |
|---|---|
| atgaagaagg agctgagctt ccacgaaaag ctgctgaagc tgactaagca gcaaaaaaag | 60 |
| aagacgaaca agcacgtttt catcgcaatc ccgatcgttt cgtcctgat gttcgctttc | 120 |
| atgtgggcag gtaaagcaga gactcctaaa gtaaaaacct acagcgacga cgtactgagc | 180 |
| gcttcttttg tgggtgatat catgatgggt cgttacgtcg agaaagtgac tgagcagaaa | 240 |
| ggtgcagata gcatcttcca gtacgttgaa ccaatcttcc gtgcttccga ttacgtggct | 300 |
| ggtaacttcg aaaacccggt aacttaccag aaaaactaca acaggcaga caaaaaaatc | 360 |
| cacctgcaga ccaacaaaga tccgttaaa gtgctgaaag acatgaactt caccgtgctg | 420 |
| aacagcgcga acaaccacgc gatggactac ggcgtgcagg gtatgaaaga tacctgggt | 480 |
| gaattcgcaa acagaaccct ggacatcgtg ggtgcaggtt actctctgtc tgacgcgaaa | 540 |
| aagaaaatct cctatcagaa agttaacggc gtgacgatcg cgactctggg tttcactgac | 600 |
| gtatctggta aaggtttcgc tgctaaaaaa acaccccgg gtgtgctgcc agctgatcct | 660 |
| gaaattttca tcccgatgat ctctgaagcg aaaaaacatg ccgacatcgt tgtcgtccag | 720 |
| tcccactggg gccaagaata tgacaacgac ccgaatgacc gtcagcgtca actggctcgt | 780 |
| gccatgtctg atgcgggcgc ggatattatt gttggccatc atccgcatgt tctggaaccg | 840 |
| attgaagttt ataatggcac tgttattttt tattctctgg gcaacttcgt atttgaccag | 900 |
| ggctggaccc gtaccgcga ttctgcgctg gttcagtatc acctgaaaaa aaatggcacc | 960 |
| ggccgctttg aagtaacccc gattgatatt cacgaagcga ccccggcccc ggttaaaaaa | 1020 |
| gatagcctga acagaaaac cattatccgc gaactgacca agattccaa ctttgcctgg | 1080 |
| aaagttgaag atggcaaact gacgtttgat atcgaccact ccgacaaact gaaatccaaa | 1140 |
| taa | 1143 |

<210> SEQ ID NO 14
<211> LENGTH: 288
<212> TYPE: DNA
<213> ORGANISM: Bacillus subtilis
<220> FEATURE:
<221> NAME/KEY: misc_feature
<222> LOCATION: (1)..(288)
<223> OTHER INFORMATION: Bacillus sp. YP1

<400> SEQUENCE: 14

| | |
|---|---|
| atggtcagag aggcagcaat gcttcacatt aaagaaggcc ttgaacaaga gtttgaggat | 60 |
| gcattccggc aagcggcgcc gattatttcc ggcatgaagg gctatatcac tcactcgtta | 120 |
| tcaaaatgca tggaggaaac gcataaatat ctgcttcttg tggagtggga aacacttgag | 180 |
| aaccatacgg aaggctttcg cggttcttca gagtatcaag agtggaaagc cttgcttcat | 240 |
| cgattctata ccccgttccc gacggtcgag cattttcagg atgtgtaa | 288 |

<210> SEQ ID NO 15
<211> LENGTH: 38
<212> TYPE: DNA
<213> ORGANISM: Artificial Sequence
<220> FEATURE:
<223> OTHER INFORMATION: Synthetic T2 F-primer

<400> SEQUENCE: 15

| | |
|---|---|
| aagaaggaga taccatgg gtatcatcaa cggtaaag | 38 |

-continued

```
<210> SEQ ID NO 16
<211> LENGTH: 40
<212> TYPE: DNA
<213> ORGANISM: Artificial Sequence
<220> FEATURE:
<223> OTHER INFORMATION: Synthetic T2 R-primer

<400> SEQUENCE: 16
gtggtggtgg tggtgctcga ttactgttcc gcatccgcgt                40

<210> SEQ ID NO 17
<211> LENGTH: 37
<212> TYPE: DNA
<213> ORGANISM: Artificial Sequence
<220> FEATURE:
<223> OTHER INFORMATION: Synthetic T4 F-primer

<400> SEQUENCE: 17
aagaaggaga taccatga cccgtagcga tttcatc                    37

<210> SEQ ID NO 18
<211> LENGTH: 39
<212> TYPE: DNA
<213> ORGANISM: Artificial Sequence
<220> FEATURE:
<223> OTHER INFORMATION: Synthetic T4 R-primer

<400> SEQUENCE: 18
gtggtggtgg tggtgctcga ttagtgatgg ctagaatgc                39

<210> SEQ ID NO 19
<211> LENGTH: 37
<212> TYPE: DNA
<213> ORGANISM: Artificial Sequence
<220> FEATURE:
<223> OTHER INFORMATION: Synthetic T5 F-primer

<400> SEQUENCE: 19
aagaaggaga taccatgc tgtttaagaa ggaccgt                    37

<210> SEQ ID NO 20
<211> LENGTH: 41
<212> TYPE: DNA
<213> ORGANISM: Artificial Sequence
<220> FEATURE:
<223> OTHER INFORMATION: Synthetic T5 R-primer

<400> SEQUENCE: 20
gtggtggtgg tggtgctcga ttattcttcg gtcagaatta c             41

<210> SEQ ID NO 21
<211> LENGTH: 37
<212> TYPE: DNA
<213> ORGANISM: Artificial Sequence
<220> FEATURE:
<223> OTHER INFORMATION: Synthetic T6 F-primer

<400> SEQUENCE: 21
aagaaggaga taccatga acgagttcat gaagaag                    37

<210> SEQ ID NO 22
<211> LENGTH: 41
<212> TYPE: DNA
<213> ORGANISM: Artificial Sequence
<220> FEATURE:
<223> OTHER INFORMATION: Synthetic T6 R-primer
```

<400> SEQUENCE: 22
gtggtggtgg tggtgctcga ttagattttg atgtcttctt g                41

<210> SEQ ID NO 23
<211> LENGTH: 37
<212> TYPE: DNA
<213> ORGANISM: Artificial Sequence
<220> FEATURE:
<223> OTHER INFORMATION: Synthetic T8 F-primer

<400> SEQUENCE: 23
aagaaggaga taccatga aaaacgacaa ccagacg                      37

<210> SEQ ID NO 24
<211> LENGTH: 39
<212> TYPE: DNA
<213> ORGANISM: Artificial Sequence
<220> FEATURE:
<223> OTHER INFORMATION: Synthetic T8 R-primer

<400> SEQUENCE: 24
gtggtggtgg tggtgctcga ttactggtgt ttgcggcct                  39

<210> SEQ ID NO 25
<211> LENGTH: 37
<212> TYPE: DNA
<213> ORGANISM: Artificial Sequence
<220> FEATURE:
<223> OTHER INFORMATION: Synthetic T9 F-primer

<400> SEQUENCE: 25
aagaaggaga taccatga agaaggagct gagcttc                      37

<210> SEQ ID NO 26
<211> LENGTH: 39
<212> TYPE: DNA
<213> ORGANISM: Artificial Sequence
<220> FEATURE:
<223> OTHER INFORMATION: Synthetic T9 R-primer

<400> SEQUENCE: 26
gtggtggtgg tggtgctcga ttatttggat ttcagtttg                  39

<210> SEQ ID NO 27
<211> LENGTH: 37
<212> TYPE: DNA
<213> ORGANISM: Artificial Sequence
<220> FEATURE:
<223> OTHER INFORMATION: Synthetic T10 F-primer

<400> SEQUENCE: 27
aagaaggaga taccatgg tcagagaggc agcaatg                      37

<210> SEQ ID NO 28
<211> LENGTH: 39
<212> TYPE: DNA
<213> ORGANISM: Artificial Sequence
<220> FEATURE:
<223> OTHER INFORMATION: Synthetic T10 R-primer

<400> SEQUENCE: 28
gtggtggtgg tggtgctcga ttacacatcc tgaaaatgc                  39